US006683319B1

(12) United States Patent
Koenck et al.

(10) Patent No.: US 6,683,319 B1
(45) Date of Patent: Jan. 27, 2004

(54) SYSTEM AND METHOD FOR IRRADIATION WITH IMPROVED DOSAGE UNIFORMITY

(75) Inventors: Steven E. Koenck, Cedar Rapids, IA (US); Stan V. Lyons, Brentwood, CA (US)

(73) Assignee: Mitec Incorporated, Cedar Rapids, IA (US)

( * ) Notice: Subject to any disclaimer, the term of this patent is extended or adjusted under 35 U.S.C. 154(b) by 0 days.

(21) Appl. No.: 10/187,294

(22) Filed: Jul. 16, 2002

Related U.S. Application Data

(60) Provisional application No. 60/306,086, filed on Jul. 17, 2001.

(51) Int. Cl.[7] .............................. H01J 3/14; A61N 5/00; G21K 5/00; G21K 5/10

(52) U.S. Cl. .............................. 250/492.3; 250/396 R; 250/398; 250/492.1; 250/492.2

(58) Field of Search ...................... 430/311; 250/396 R, 250/398, 492.1, 492.2, 492.3

(56) References Cited

U.S. PATENT DOCUMENTS

| | | | | |
|---|---|---|---|---|
| 924,284 | A | 6/1909 | Smith | |
| 1,809,078 | A | 6/1931 | Smith | |
| 2,095,502 | A | 10/1937 | Johnston | 21/54 |
| 2,456,909 | A | 12/1948 | Brasch | 21/54 |
| 2,602,751 | A | 7/1952 | Robinson | 99/221 |
| 2,741,704 | A | 4/1956 | Trump et al. | 250/49.5 |
| 2,816,231 | A | 12/1957 | Nygard | 250/43 |
| 2,824,969 | A | 2/1958 | Crowley-Milling | 250/49.5 |
| 2,963,369 | A | 12/1960 | Urbain | 99/107 |
| 2,989,735 | A | 6/1961 | Gumpertz | 340/174.1 |
| 3,087,598 | A | 4/1963 | Clore | 198/38 |
| 3,224,562 | A | 12/1965 | Bailey et al. | 198/131 |
| 3,261,140 | A | 7/1966 | Long et al. | 53/22 |
| 3,396,273 | A | 8/1968 | Brunner | 250/52 |
| 3,452,195 | A | 6/1969 | Brunner | 250/52 |
| 3,560,745 | A | 2/1971 | Peterson et al. | 250/83 |
| 3,564,241 | A | 2/1971 | Ludwig | 250/52 |
| 3,567,462 | A | 3/1971 | Silverman et al. | 99/157 |
| 3,676,673 | A | 7/1972 | Coleman | 250/49.5 |
| 3,676,678 | A | 7/1972 | Ransohoff et al. | 250/52 |
| 3,780,305 | A | 12/1973 | Free | 250/400 |
| 3,876,373 | A | 4/1975 | Glyptis | 21/54 |
| 3,974,391 | A | 8/1976 | Offermann | 250/492 |
| 4,013,261 | A | 3/1977 | Steigerwald et al. | 250/453 |
| 4,066,907 | A | 1/1978 | Tetzlaff | 250/453 |
| 4,151,419 | A | 4/1979 | Morris et al. | 250/453 |
| 4,201,920 | A | 5/1980 | Tronc et al. | 250/492 |
| 4,281,251 | A | 7/1981 | Thompson et al. | 250/398 |
| 4,484,341 | A | 11/1984 | Luniewski | 378/69 |
| 4,633,090 | A | * 12/1986 | Hahn | 250/492.2 |
| 4,652,763 | A | 3/1987 | Nablo | 250/492.3 |
| 4,663,532 | A | 5/1987 | Roche | 250/400 |
| 4,757,201 | A | 7/1988 | Kanter | 250/337 |
| 4,760,264 | A | 7/1988 | Barrett | 250/453.1 |
| 4,767,930 | A | 8/1988 | Stieber et al. | 250/396 |
| 4,785,178 | A | 11/1988 | Lynch et al. | 250/496.1 |
| 4,788,126 | A | 11/1988 | Feldman et al. | 430/138 |
| 4,788,701 | A | 11/1988 | Barrett | 378/69 |
| 4,852,138 | A | 7/1989 | Bergeret et al. | 378/69 |
| 4,864,595 | A | 9/1989 | Barrett | 378/69 |
| 4,866,281 | A | 9/1989 | Bosshard | 250/453.1 |
| 4,870,368 | A | 9/1989 | Putnam | 328/233 |
| 4,908,221 | A | 3/1990 | Barrett | 426/240 |
| 4,974,503 | A | 12/1990 | Koch | 99/451 |
| 5,004,926 | A | 4/1991 | Vassenaix et al. | 250/492.3 |
| 5,008,550 | A | 4/1991 | Barrett | 250/453.1 |

(List continued on next page.)

*Primary Examiner*—John R. Lee
*Assistant Examiner*—Mary El-Shammaa
(74) *Attorney, Agent, or Firm*—Kinney & Lange, P.A.

(57) ABSTRACT

A system and method for providing irradiation to material shapes an electron beam into a profile having a substantially rectangular intensity distribution. The profile is deflected onto the material in a pattern with substantial overlap in a first dimension and without substantial overlap in a second dimension. In an exemplary embodiment, irradiation is provided to the material from first and second opposite sides.

25 Claims, 10 Drawing Sheets

U.S. PATENT DOCUMENTS 5,026,983 A 6/1991 Meyn ..................... 250/233 R
5,096,553 A 3/1992 Ross et al. ............. 204/157.15
5,101,168 A 3/1992 Miller ........................ 328/233
5,323,442 A 6/1994 Golovanivsky et al. ..... 378/119
5,362,442 A 11/1994 Kent ........................... 422/22
5,366,746 A 11/1994 Mendenhall ................ 426/521
5,396,071 A 3/1995 Atwell et al. ............ 250/358.1
5,396,074 A 3/1995 Peck et al. ............. 250/453.11
5,400,382 A 3/1995 Welt et al. .................... 378/69
5,434,421 A 7/1995 Burth ......................... 250/434
5,439,781 A * 8/1995 MacDowell et al. ........ 430/311
5,449,916 A * 9/1995 Smyth et al. ............... 250/398
5,451,790 A 9/1995 Enge .......................... 250/436
5,461,656 A 10/1995 Golovanivsky et al. ....... 378/66
5,470,597 A 11/1995 Mendenhall ................ 426/521
5,482,726 A 1/1996 Robinson, Jr. .............. 426/238
5,530,255 A 6/1996 Lyons et al. ............. 250/492.3
5,554,856 A 9/1996 Bidnyy et al. .............. 250/455
5,557,109 A 9/1996 Bidnyy et al. .............. 250/455
5,590,602 A 1/1997 Peck et al. ............... 104/88.01
5,593,713 A 1/1997 De La Luz-Martinez et al. .......................... 426/237
5,597,597 A 1/1997 Newman .................... 426/248
5,603,972 A 2/1997 McFarland .................. 426/240
5,635,714 A 6/1997 Nablo et al. ................ 250/305
5,661,305 A 8/1997 Lawrence et al. .......... 250/397
5,690,978 A 11/1997 Yin et al. ................... 426/237
5,757,009 A * 5/1998 Walstrom ............... 250/396 R
5,801,387 A 9/1998 Nablo et al. ............. 250/492.3
5,834,744 A 11/1998 Risman ...................... 219/697
5,838,760 A 11/1998 Moses ........................ 378/119
5,847,401 A 12/1998 McKeown et al. ......... 250/396
5,881,534 A 3/1999 Ahlqvist et al. .............. 53/403
5,994,706 A 11/1999 Allen et al. ............ 250/454.11
6,023,497 A 2/2000 Takahashi et al. ............ 378/57
6,027,754 A 2/2000 Bushnell et al. ............ 426/238
6,051,185 A 4/2000 Beers .......................... 422/22
6,066,348 A 5/2000 Yuan et al. ................. 426/236
6,086,932 A 7/2000 Gupta ........................ 426/237
6,096,379 A 8/2000 Eckhoff ...................... 427/428
6,127,687 A 10/2000 Williams et al. ......... 250/492.3
6,429,444 B1 8/2002 Korenev et al. ......... 250/492.3
6,486,482 B1 * 11/2002 Anderberg et al. ...... 250/492.3

* cited by examiner

| | | | | | | | | | | | | | | | | | | | | |
|---|---|---|---|---|---|---|---|---|---|---|---|---|---|---|---|---|---|---|---|---|
| 0.25 | 0.29 | 0.33 | 0.36 | 0.40 | 0.43 | 0.45 | 0.47 | 0.49 | 0.50 | 0.50 | 0.50 | 0.49 | 0.47 | 0.45 | 0.43 | 0.40 | 0.36 | 0.33 | 0.29 | 0.25 |
| 0.29 | 0.33 | 0.38 | 0.42 | 0.46 | 0.49 | 0.52 | 0.55 | 0.56 | 0.57 | 0.58 | 0.57 | 0.56 | 0.55 | 0.52 | 0.49 | 0.46 | 0.42 | 0.38 | 0.33 | 0.29 |
| 0.33 | 0.38 | 0.43 | 0.48 | 0.52 | 0.56 | 0.59 | 0.62 | 0.64 | 0.65 | 0.65 | 0.65 | 0.64 | 0.62 | 0.59 | 0.56 | 0.52 | 0.48 | 0.43 | 0.38 | 0.33 |
| 0.36 | 0.42 | 0.48 | 0.53 | 0.58 | 0.62 | 0.66 | 0.69 | 0.71 | 0.72 | 0.73 | 0.72 | 0.71 | 0.69 | 0.66 | 0.62 | 0.58 | 0.53 | 0.48 | 0.42 | 0.36 |
| 0.40 | 0.46 | 0.52 | 0.58 | 0.63 | 0.68 | 0.72 | 0.75 | 0.77 | 0.79 | 0.79 | 0.79 | 0.77 | 0.75 | 0.72 | 0.68 | 0.63 | 0.58 | 0.52 | 0.46 | 0.40 |
| 0.43 | 0.49 | 0.56 | 0.62 | 0.68 | 0.73 | 0.77 | 0.81 | 0.83 | 0.85 | 0.85 | 0.85 | 0.83 | 0.81 | 0.77 | 0.73 | 0.68 | 0.62 | 0.56 | 0.49 | 0.43 |
| 0.45 | 0.52 | 0.59 | 0.66 | 0.72 | 0.77 | 0.82 | 0.86 | 0.88 | 0.90 | 0.90 | 0.90 | 0.88 | 0.86 | 0.82 | 0.77 | 0.72 | 0.66 | 0.59 | 0.52 | 0.45 |
| 0.47 | 0.55 | 0.62 | 0.69 | 0.75 | 0.81 | 0.86 | 0.89 | 0.92 | 0.94 | 0.95 | 0.94 | 0.92 | 0.89 | 0.86 | 0.81 | 0.75 | 0.69 | 0.62 | 0.55 | 0.47 |
| 0.49 | 0.56 | 0.64 | 0.71 | 0.77 | 0.83 | 0.88 | 0.92 | 0.95 | 0.97 | 0.98 | 0.97 | 0.95 | 0.92 | 0.88 | 0.83 | 0.77 | 0.71 | 0.64 | 0.56 | 0.49 |
| 0.50 | 0.57 | 0.65 | 0.72 | 0.79 | 0.85 | 0.90 | 0.94 | 0.97 | 0.99 | 0.99 | 0.99 | 0.97 | 0.94 | 0.90 | 0.85 | 0.79 | 0.72 | 0.65 | 0.57 | 0.50 |
| 0.50 | 0.58 | 0.65 | 0.73 | 0.79 | 0.85 | 0.90 | 0.95 | 0.98 | 0.99 | 1.00 | 0.99 | 0.98 | 0.95 | 0.90 | 0.85 | 0.79 | 0.73 | 0.65 | 0.58 | 0.50 |
| 0.50 | 0.57 | 0.65 | 0.72 | 0.79 | 0.85 | 0.90 | 0.94 | 0.97 | 0.99 | 0.99 | 0.99 | 0.97 | 0.94 | 0.90 | 0.85 | 0.79 | 0.72 | 0.65 | 0.57 | 0.50 |
| 0.49 | 0.56 | 0.64 | 0.71 | 0.77 | 0.83 | 0.88 | 0.92 | 0.95 | 0.97 | 0.98 | 0.97 | 0.95 | 0.92 | 0.88 | 0.83 | 0.77 | 0.71 | 0.64 | 0.56 | 0.49 |
| 0.47 | 0.55 | 0.62 | 0.69 | 0.75 | 0.81 | 0.86 | 0.89 | 0.92 | 0.94 | 0.95 | 0.94 | 0.92 | 0.89 | 0.86 | 0.81 | 0.75 | 0.69 | 0.62 | 0.55 | 0.47 |
| 0.45 | 0.52 | 0.59 | 0.66 | 0.72 | 0.77 | 0.82 | 0.86 | 0.88 | 0.90 | 0.90 | 0.90 | 0.88 | 0.86 | 0.82 | 0.77 | 0.72 | 0.66 | 0.59 | 0.52 | 0.45 |
| 0.43 | 0.49 | 0.56 | 0.62 | 0.68 | 0.73 | 0.77 | 0.81 | 0.83 | 0.85 | 0.85 | 0.85 | 0.83 | 0.81 | 0.77 | 0.73 | 0.68 | 0.62 | 0.56 | 0.49 | 0.43 |
| 0.40 | 0.46 | 0.52 | 0.58 | 0.63 | 0.68 | 0.72 | 0.75 | 0.77 | 0.79 | 0.79 | 0.79 | 0.77 | 0.75 | 0.72 | 0.68 | 0.63 | 0.58 | 0.52 | 0.46 | 0.40 |
| 0.36 | 0.42 | 0.48 | 0.53 | 0.58 | 0.62 | 0.66 | 0.69 | 0.71 | 0.72 | 0.73 | 0.72 | 0.71 | 0.69 | 0.66 | 0.62 | 0.58 | 0.53 | 0.48 | 0.42 | 0.36 |
| 0.33 | 0.38 | 0.43 | 0.48 | 0.52 | 0.56 | 0.59 | 0.62 | 0.64 | 0.65 | 0.65 | 0.65 | 0.64 | 0.62 | 0.59 | 0.56 | 0.52 | 0.48 | 0.43 | 0.38 | 0.33 |
| 0.29 | 0.33 | 0.38 | 0.42 | 0.46 | 0.49 | 0.52 | 0.55 | 0.56 | 0.57 | 0.58 | 0.57 | 0.56 | 0.55 | 0.52 | 0.49 | 0.46 | 0.42 | 0.38 | 0.33 | 0.29 |
| 0.25 | 0.29 | 0.33 | 0.36 | 0.40 | 0.43 | 0.45 | 0.47 | 0.49 | 0.50 | 0.50 | 0.50 | 0.49 | 0.47 | 0.45 | 0.43 | 0.40 | 0.36 | 0.33 | 0.29 | 0.25 |

FIG. 4
PRIOR ART

SYSTEM AND METHOD FOR IRRADIATION WITH IMPROVED DOSAGE UNIFORMITY

CROSS-REFERENCE TO RELATED APPLICATION(S)

This application claims the benefit of U.S. Provisional Application No. 60/306,086 filed Jul. 17, 2001 for "System and Method for Two Sided Irradiation With Improved Dosage Uniformity" by S. Lyons and S. Koenck.

INCORPORATION BY REFERENCE

The aforementioned U.S. Provisional Application No. 60/306,086 is hereby incorporated by reference in its entirety.

BACKGROUND OF THE INVENTION

The present invention relates to an irradiation system, and more particularly to a system and method for irradiating product in a manner that improves the uniformity of the irradiation dose delivered to the product.

Irradiation technology for medical and food sterilization has been scientifically understood for many years dating back to the 1940's. The increasing concern for food safety as well as safe, effective medical sterilization has resulted in growing interest and recently expanded government regulatory approval of irradiation technology for these applications. United States Government regulatory agencies have recently approved the use of irradiation processing of red meat in general and ground meat in particular. Ground meat such as ground beef is of particular concern for risk of food borne illness due to the fact that contaminants introduced during processing may be mixed throughout the product including the extreme product interior which receives the least amount of heat during cooking. Irradiation provides a very effective means of reducing the population of such harmful pathogens.

Various types of radiation sources are approved for the treatment of food products including gamma sources such as radioactive cobalt 60, accelerated electrons with energy up to 10 MeV, and x-rays from electron accelerators of up to 5 MeV. Electron beam and x-ray machine generated sources are becoming increasingly popular due to their flexibility and a general consumer preference to avoid radioactive materials.

The beneficial effects of irradiation of food are caused by the absorption of ionizing energy that results in the breaking of a small percentage of the molecular bonds of molecules in the product. Most of the molecules in food are relatively small and are therefore unaffected. The DNA in bacteria, however, is a very large molecule and is highly likely to be broken and rendered unable to replicate.

FIG. 1 is a graph of exemplary percentage depth-dose curves showing the reduction of radiation intensity due to absorption of radiation in water (which is a relatively accurate model for radiation absorption in food products). Curve 10 is a percentage depth-dose curve for 1.8 MeV electrons, curve 12 is a percentage depth-dose curve for 4.7 MeV electrons, and curve 14 is a percentage depth-dose curve for 10.6 MeV electrons. For all of the electron energies, the radiation intensity increases to a maximum at a distance somewhat interior to the surface of the product due to scatter emission of radiation from electron collisions with food molecules. After the maximum is achieved, absorption causes the relative intensity to begin to fall off until virtually all of the radiation has been absorbed. At the "tails" of the depth-dose chart the intensity is much less than the maximum, but still results in an incremental amount of beneficial irradiation. Single sided application of radiation that is required to maintain a moderate ratio between maximum and minimum exposure must necessarily waste most of this tail of radiation intensity.

Curve 12 of FIG. 1 illustrates that the percentage depth-dose for 4.7 MeV electrons is approximately 50% of its maximum value at a penetration depth of about 2.0 centimeters or 0.8 inches. Exposure of food of this thickness would result in a maximum/minimum dose ratio of 1/0.5=2.0. The portion of the beam power that is not absorbed would pass through the material and be wasted. The preferred solution to this inefficient use of the ionizing radiation is to expose the product to the electron beam from two sides. FIG. 2 is a graph of an exemplary depth-dose curve for two sided 4.7 MeV exposure of product having a 4.0 centimeter or 1.57 inch thickness. The depth exposed is substantially greater than for single sided exposure, and the maximum/minimum ratio is substantially lower, resulting in more precise and consistent product exposure.

While two sided irradiation is preferred for maximum efficiency and most consistent exposure, generation of two sided radiation can be problematic. The typical solutions are to either pass product through the radiation source once per side, which requires twice as long to process and may not be viable for products that cannot be flipped over due to material redistribution, or to create two independent accelerators which is costly and complex.

Electron accelerators of several types are known in the art. A preferred electron accelerator for irradiation applications is the well known linear accelerator or LINAC, which employs a high power microwave source driving a specially constructed waveguide to accelerate electrons by electromagnetic induction. A preferred LINAC operation methodology is pulsed operation, whereby a relatively short, high intensity pulse of accelerated electrons is generated at a selected repetition rate. The timing and magnitude of this pulse of accelerated electrons may be controlled by a computer control system.

The stream of accelerated electrons emerging from a typical LINAC is concentrated into a narrow beam approximately 0.5 centimeters in diameter, which is much too small and intense to apply directly to material to be processed. Prior art systems typically shape and spread the beam by passing it through a quadrupole magnet which spreads the beam in both the vertical and horizontal dimensions in a manner analogous to an optical lens. FIG. 3 is a diagram illustrating a typical spread beam intensity distribution, which takes the shape of elliptical profile 20. The intensity profile corresponds generally to bell shaped distributions 24 and 26 centered about the vertical and horizontal axes of symmetry. Line 22 surrounding elliptical profile 20 corresponds to the points where the intensity is at halfpower (or −3 db) from maximum. A two-dimensional bell shaped distribution corresponding to a normalized raised cosine function:

$$f(x,y)=(1+\cos(x))*(1+\cos(y))/4$$

is represented numerically by the table shown in FIG. 4.

Prior art irradiation systems, such as the system disclosed in published PCT Application No. WO01/26135 filed by Mitec Incorporated, the same assignee as the present application, apply a series of 50% overlapping pulses of accelerated electrons formed in an intensity profile according to the elliptical pattern shown in FIGS. 3 and 4. Various points in FIG. 4 are shown with a box around them, including the center point with normalized intensity of 1.00, the 25% points (halfway between the center point and the 0.50 intensity points) with a normalized intensity of 0.73, and a set of points forming a generally elliptical shape surrounding the center point. These points represent normalized intensity values between 0.47 and 0.53 (approximately −3 db) and correspond generally to the elliptical shape shown in FIG. 3. A 50% overlap results in a constant intensity distribution along the axis of symmetry. With 50% overlap in both the vertical and horizontal dimensions, the resultant two dimensional exposure is four times the single pulse peak exposure. This distribution, however, is not exactly constant off the axes of symmetry. The greatest deviation is observed at the 25% points. With 50% overlapping vertical and horizontal exposure, the normalized exposure at these points is:

$$0.73 \times 4 = 3.44$$

which is 14% less than the nominal "on-axis" exposure. When an important performance criterion for irradiation exposure is uniformity of dose, this exposure variation contributes directly to an increased maximum/minimum dose ratio, and is undesirable.

FIG. 5 is a schematic diagram illustrating a single accelerator, two sided irradiation system 30 having a structure similar to that disclosed in published PCT Application No. WO01/26135. Irradiation system 30 includes quadrupole magnet 32, upper deflection magnet 34 and lower deflection magnet 36 for direction of electrons toward material 38. The paths that accelerated electrons may be directed by relatively constant currents in deflection magnets 34 and 36 from a single accelerator to two sides of material to be processed are illustrated by dotted lines. A benefit of the system of FIG. 5 is that relatively few magnets are required to direct the accelerated electrons to the two opposite sides of material. There is, however, a substantial difference in the path lengths that electrons must travel from deflection magnets 34 and 36 to material 38 being processed. Since deflection electromagnets operate on accelerated electrons by displacing their path in an angle proportional to the magnetic field, the field required to deflect electrons to a selected position must be set to a predetermined value. This predetermined value may be controlled by a computer driving a relatively constant current into the magnet to direct the electrons to the correct location. Unfortunately, if the beam spot is formed by a typical quadrupole magnet such as quadrupole magnet 32, the formed elliptical beam spot consists of diverging rays of electron paths, so the elliptical spot will be larger in an amount proportional to the path length. In the illustration of FIG. 5, an exemplary physical size for the total height of the apparatus may be 72 inches or more, so the path length may vary from as little as 24 inches for the inner downward path to more than 100 inches for the outer upward path. This 4:1 length ratio would cause a corresponding 4:1 increase in the beam divergence and resulting elliptical spot size. The increased spot size may be so large that the width of the scan horn (not shown in FIG. 5) may have to be increased to provide an unrestricted path for the accelerated electrons to be directed to material 38 to be processed. The scan horn is typically constructed of very rigid stainless steel and provides a high vacuum environment for the propagation of electrons with minimum attenuation. It is desirable for the interior volume of the scan horn to be minimized to minimize the required vacuum pump capacity It would be desirable to provide a system for applying radiation to two opposite sides of articles from a single radiation source with precise uniformity of the dose applied to the articles. The present invention is a cost effective method and apparatus utilizing a single pulsed accelerated electron source and simple electron beam manipulation elements to process, form and direct a stream of electrons to material to be processed with controlled, uniform dosage.

BRIEF SUMMARY OF THE INVENTION

The present invention is a system and method for providing irradiation to material. An electron beam is shaped into a profile having a substantially rectangular intensity distribution. The profile is deflected onto the material in a pattern with substantial overlap in a first dimension and without substantial overlap in a second dimension. In an exemplary embodiment, irradiation is provided to the material from first and second opposite sides.

BRIEF DESCRIPTION OF THE DRAWINGS

FIG. 4 is a table numerically representing a two-dimensional bell shaped distribution corresponding to a normalized raised cosine function.

DETAILED DESCRIPTION

Figure 5:
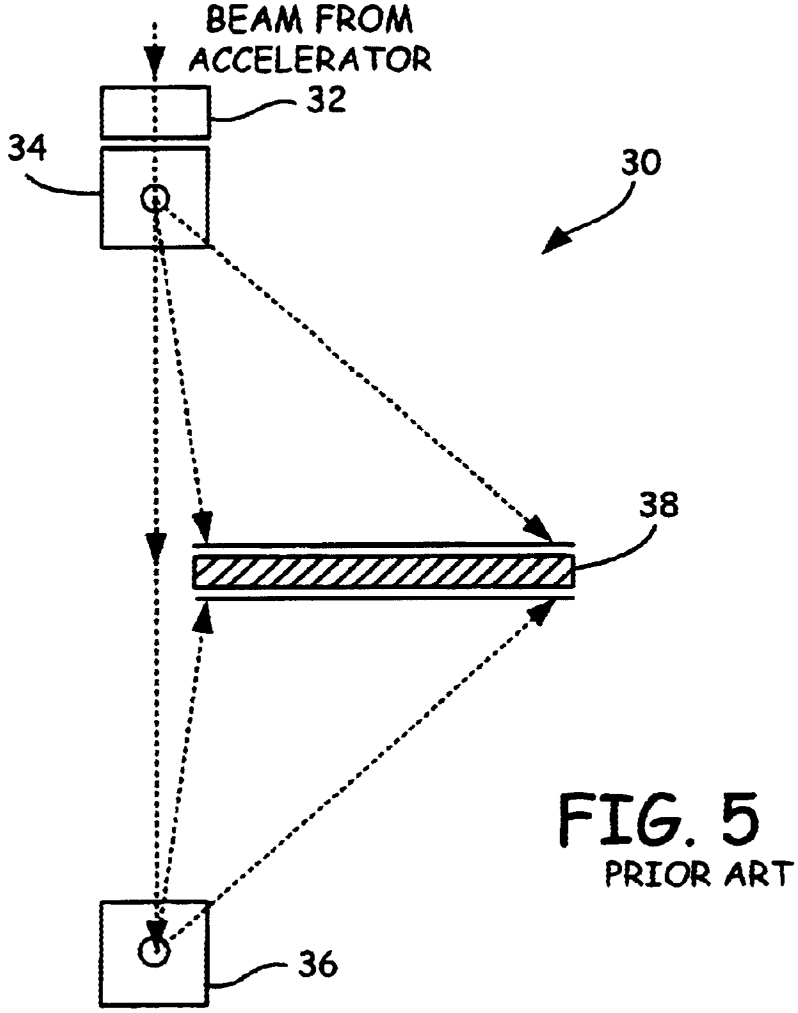
FIG. 5 PRIOR ART
FIG. 5 is a schematic diagram illustrating a single accelerator, two sided irradiation system according to the prior art.

As noted previously with respect to the prior art irradiation system of FIG. 5, the paths for accelerated electrons may be established by driving appropriate relatively constant currents into upper and lower deflection magnets, so that when a pulse of accelerated electrons is inserted into the quadrupole magnet and subsequently deflected, the elliptical spot is directed toward the product to be processed. The disadvantages of this system are the non-uniformity of dose due to the overlapping elliptical intensity profile and the divergence of the spot size at the target.

Figure 6:
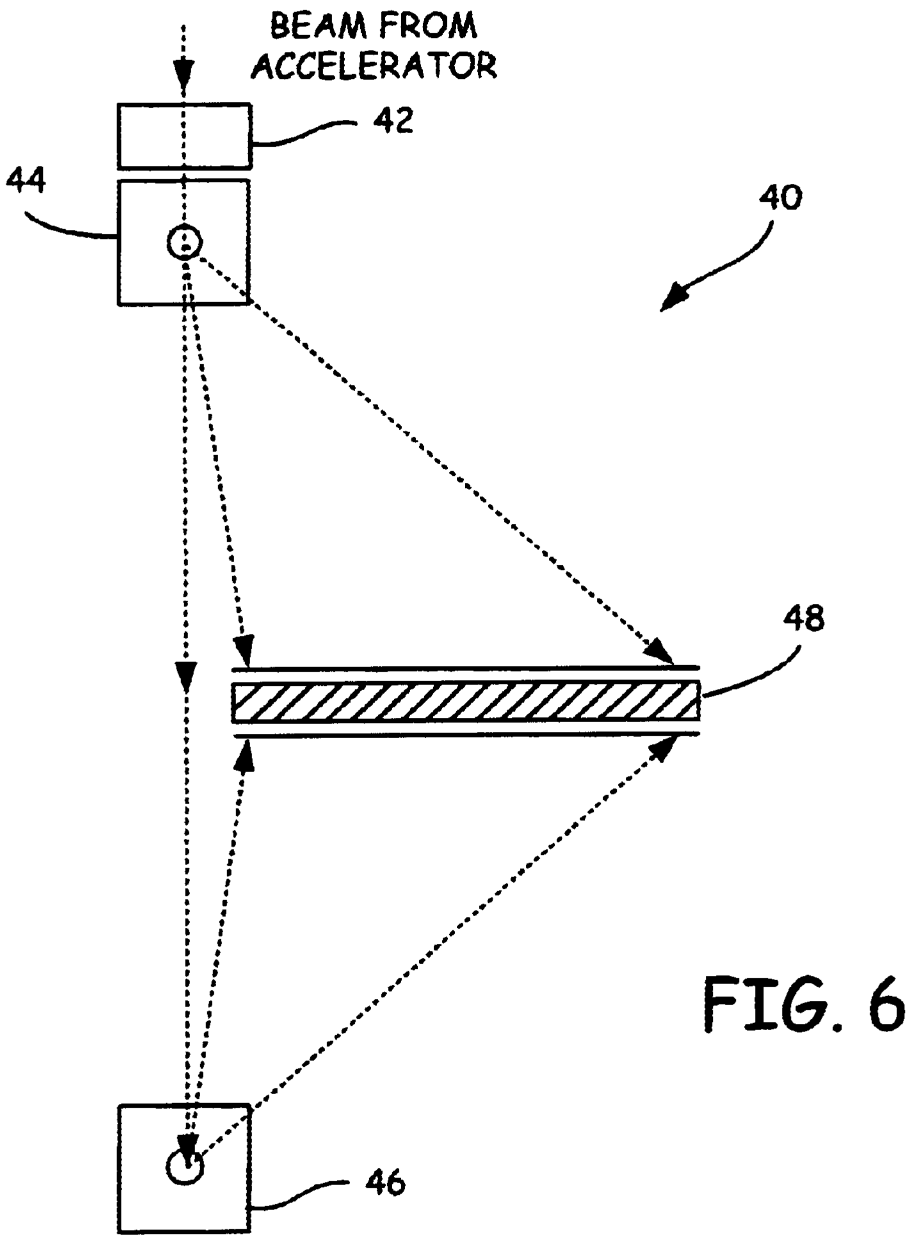
FIG. 6 is a schematic diagram illustrating a single accelerator, two sided irradiation system for practicing the present invention.
Figure 7:
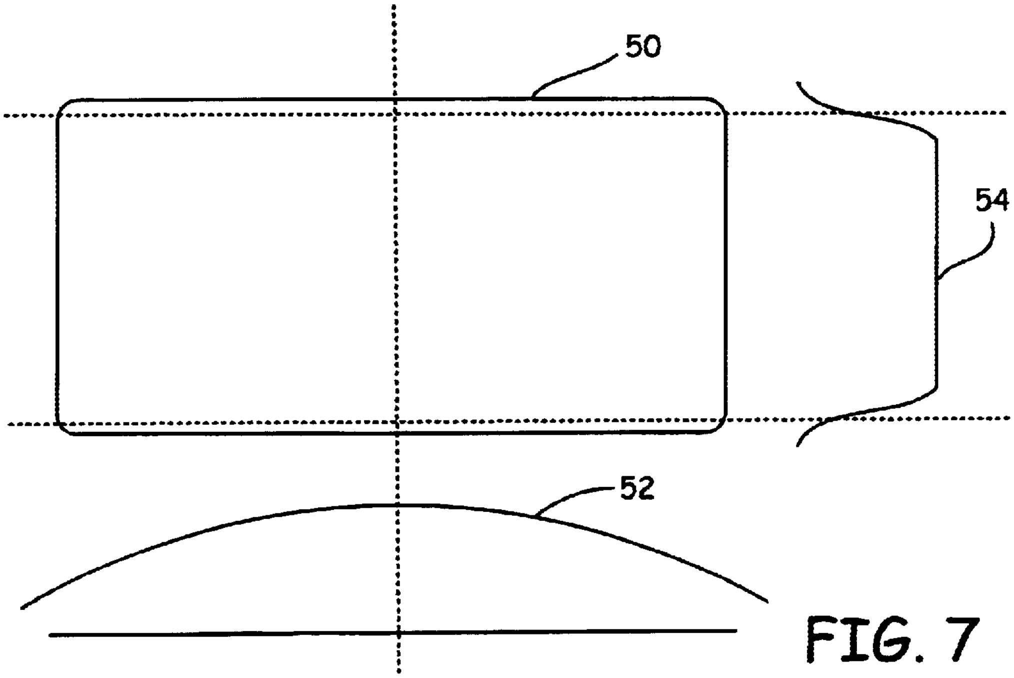
FIG. 7 is a diagram illustrating a substantially rectangular intensity distribution profile that can be produced by the system shown in FIG. 6.

A solution to this non-uniformity of intensity is to create a relatively rectangular intensity distribution profile to expose successive areas of material to be irradiated. FIG. 6 is a schematic diagram illustrating single accelerator, two sided irradiation system 40 for practicing the present invention, and FIG. 7 is a diagram illustrating rectangular intensity distribution profile 50 that can be produced by the system shown in FIG. 6. In the apparatus of FIG. 6 for producing a rectangular exposure profile, the quadrupole magnet of the prior art is replaced by duopole magnet 42. Upper deflection magnet 44 and lower deflection magnet 46 are similar to their counterparts shown in the prior art system of FIG. 5. The beam from the accelerator is provided in irradiation system 40 in a slightly different fashion than in the prior art system (as will be described in detail below with respect to FIGS. 9–12). In the horizontal direction, the exposure intensity corresponds to symmetrical bell shaped distribution 52 generally characterized by the previously described raised cosine distribution:

$$f(x)=(1+\cos(x))/2$$

Figure 1:
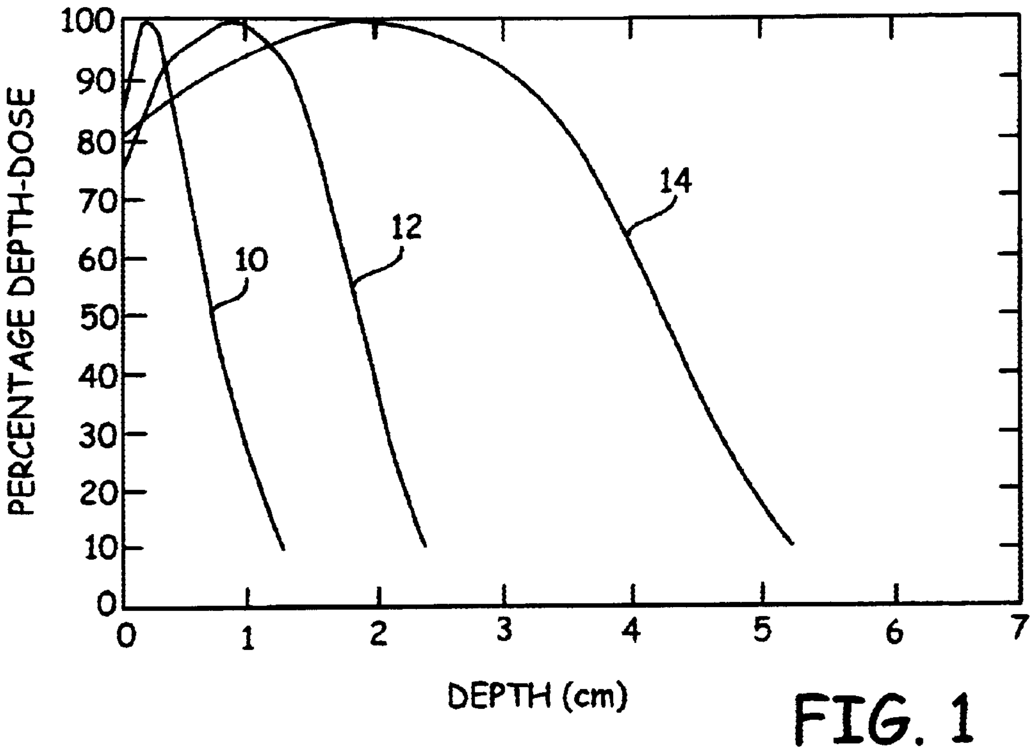
FIG. 1 is a graph of exemplary percentage depth-dose curves showing the reduction of radiation intensity due to absorption of radiation in water.
Figure 2:
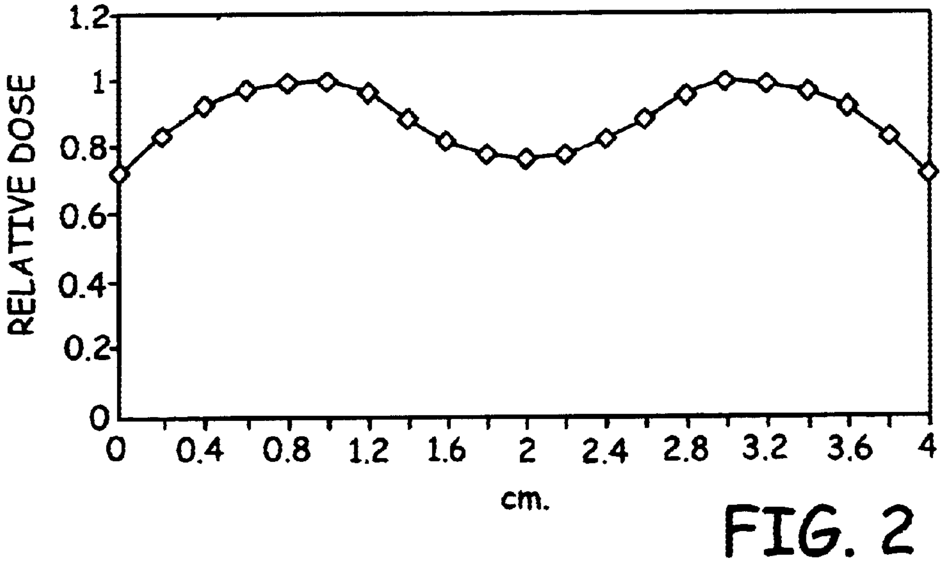
FIG. 2 is a graph of an exemplary depth-dose curve for two sided exposure of product.
Figure 3:
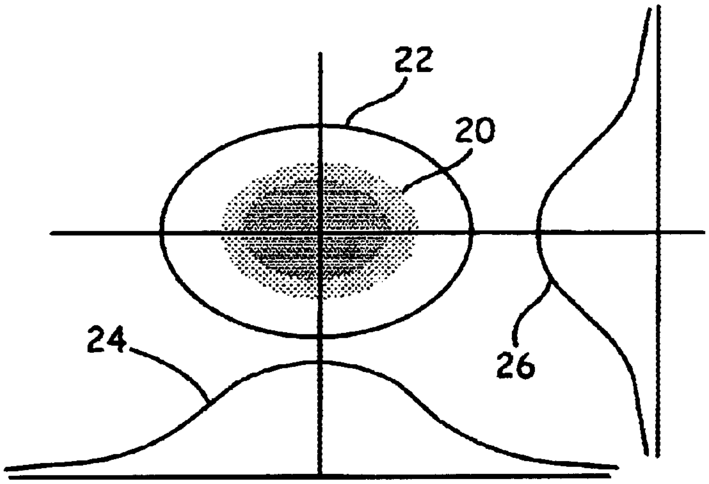
FIG. 3 PRIOR ART
FIG. 3 is a diagram illustrating a typical spread beam intensity distribution, which takes the shape of an elliptical profile.

The outline of rectangular profile 50 represents the points where intensity is at half power (or −3 db) from maximum, similar to the outline of the elliptical spot shown in FIG. 3. In the vertical direction, however, exposure intensity distribution 54 is relatively constant for any given horizontal position x. There is a necessary edge intensity rolloff function at the top and bottom of the rectangular profile as the intensity is reduced from the relatively constant value to near zero.

Figure 8:
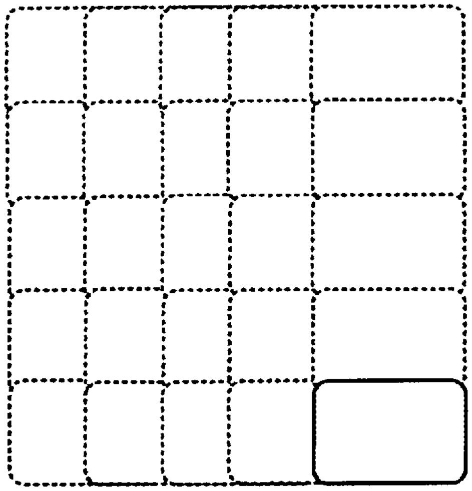
FIG. 8 is a diagram illustrating the overlapping exposure pattern of successive irradiation profiles of the present invention.

The overlap function for this specially formed rectangular intensity profile is quite different from the prior art elliptical spot intensity function. The goal of the overlap function is to achieve uniform intensity in the overlap region. In the horizontal dimension, the overlap is ideally 50% which yields a constant, uniform summation function. In the vertical dimension, the ideal overlap would be 0% if the edge intensity rolloff were an ideal square edge. FIG. 8 is a diagram illustrating this ideal overlapping exposure. With no overlap, the square edges of every other pulse could be lined up so that they just touch. If this were the case, the intensity in the vertical dimension would also be exactly constant, which is the goal for uniform dose application. In actual applications, however, it is recognized that such an ideal condition is typically not feasible for several reasons. First, it is not practical to create a square edge intensity function for the profile of the beam intensity. Second, even if it were, it is difficult to position these edges exactly adjacent to each other to achieve the desired uniformity.

A solution to the vertical overlap problem is to create an edge rolloff function similar to the previously described raised cosine function, but with a much steeper rolloff. This creates a local area of finite width that allows for a certain amount of overlap error without contributing greatly to non-uniformity of exposure. An exemplary two-dimensional overlap pattern has substantial overlap in the horizontal direction, typically 50% or more, and insubstantial overlap in the vertical direction, typically 25% or less. Such an overlap pattern, in combination with the substantially rectangular intensity distribution profile, yields improved uniformity of dosage delivered to the material being processed.

Figure 9A:
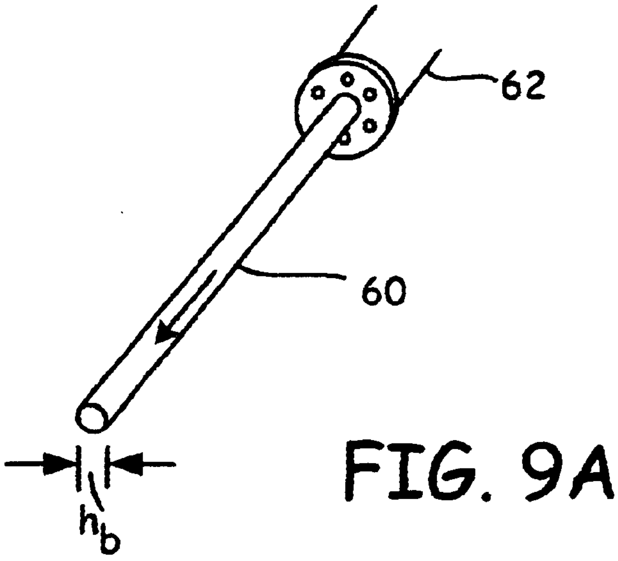
FIGS. 9A–9C are diagrams illustrating the electron beam forming and manipulation steps for creating the substantially rectangular intensity distribution profile shown in FIG. 7.
Figure 9B:
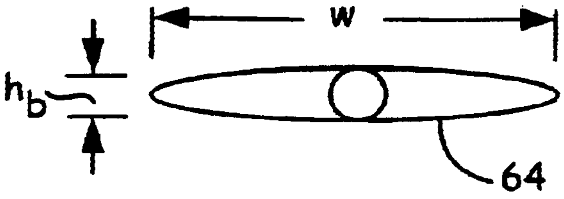
Figure 9C:
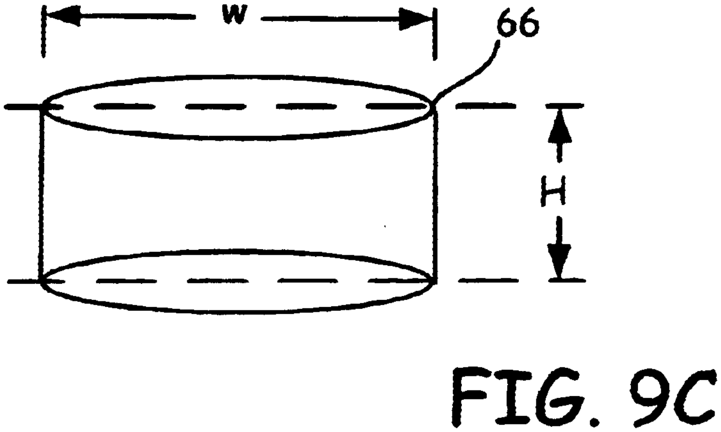

The creation of the rectangular intensity distribution profile as illustrated in FIG. 7 involves several electron beam forming and manipulation steps. FIGS. 9A–9C are diagrams illustrating these steps. Accelerated electron beam 60 of relatively monoenergetic electrons is emitted from linear accelerator 62 as is shown in FIG. 9A. Concentrated electron beam 60 emitted from linear accelerator 62 has a relatively small diameter $h_b$ (approximately 0.5 cm), and the profile of the beam is generally similar to the desired raised cosine function, although much smaller. Electron beam 60 is passed through a duopole magnet structure (such as duopole magnet 42, FIG. 6) with shaped poles to deflect the electron beam in the horizontal direction to a width W as shown in FIG. 9B. The result is that the electron beam is spread into stripe 64 with a height $h_b$ that is approximately the same as the incident electron beam from the linear accelerator, and with a width W determined by the magnet structure and its associated electromagnetic deflection.

The next step in creating the desired rectangular intensity profile is to form the vertical distribution of the profile. Rather than employ the prior art quadrupole structure to create an elliptical spot profile, a vertical "sweep" methodology is used. This is made possible by the fact that the electron beam is actually a pulse of accelerated electrons of a known predetermined length of time. It is possible to apply a rapidly changing magnetic field to horizontal stripe 64 of electrons to cause it to physically move in the vertical direction an amount H as is shown in FIG. 9C. If the magnetic field changes linearly with respect to time, the desired rectangular intensity profile 66 with relatively constant vertical intensity is created.

It will be understood by those skilled in the art that intensity profile 66 is not exactly rectangular in shape. The benefits of the present invention are achieved for any profile shape that is substantially rectangular. In the context of the present invention, a profile shape is considered substantially rectangular if the height (H) of the profile (H) is at least twice as large as the diameter ($h_b$) of the electron beam (which is also the height of the electron stripe that is vertically swept to form the substantially rectangular profile).

Figure 10:
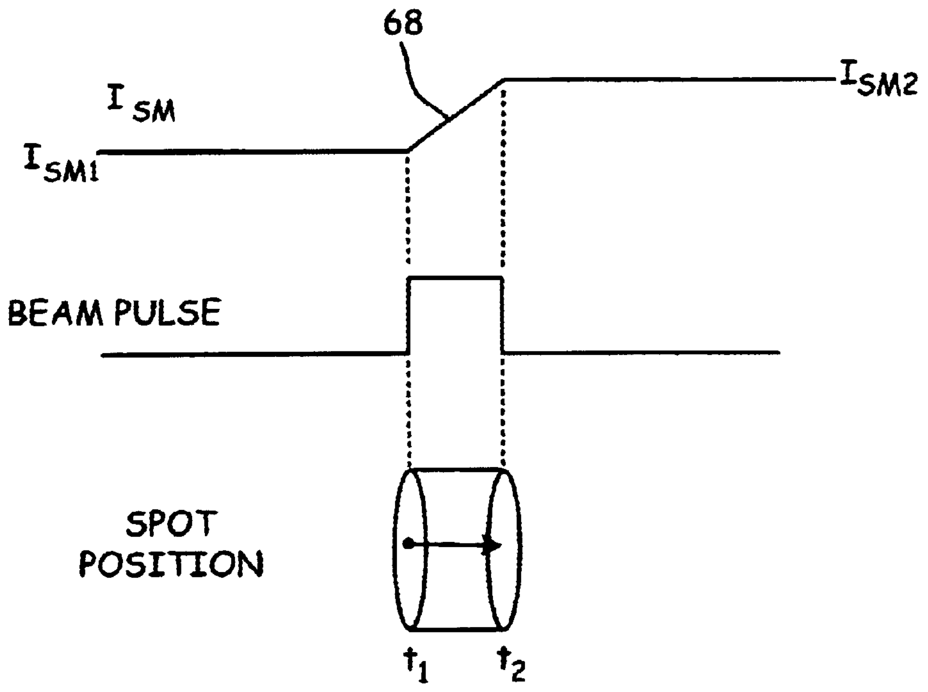
FIG. 10 is a diagram illustrating the timing and control signals associated with the sweep methodology of the present invention.

FIG. 10 is a diagram illustrating the timing and control signals associated with the above-described sweep methodology. The electron beam pulse of predetermined width is generated by the linear accelerator and is timed by the control computer. Initiation of the electron beam pulse produces a horizontal stripe, since the electron beam is spread by an appropriate magnet structure. At the same time $t_1$ that the electron beam pulse is initiated, the control computer commands a current $I_{SM}$ to be driven into the scan deflection magnet that is ramped up linearly in sloped region 68 from an initial value $I_{SM1}$ at time $t_1$ to a final value $I_{SM2}$ which it reaches at time $t_2$. The deflection of the electron beam stripe is proportional to the magnet current, so the resulting intensity profile will be nearly constant in the deflected direction.

It is desirable to be able to adjust the actual size of the intensity profile to account for size variations due to divergent radial deflection and differences in path length. This capability is provided in the present system by separate vertical and horizontal control methods.

As was explained in the description of FIG. 9B, a duopole magnet (shown in FIG. 6) with shaped pole pieces spreads the electron spot in the horizontal direction into a stripe with a width W by the application of a shaped magnet field. The amount of the horizontal spreading is controlled by the magnitude of the current in the duopole magnet, so its width W can be controlled dynamically with a computer controlled duopole magnet current driver.

Figure 11A:
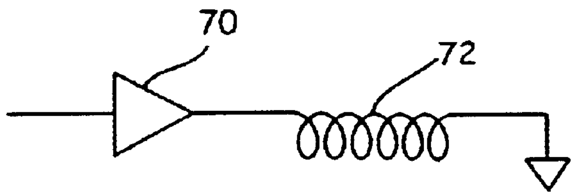
FIG. 11A is a schematic diagram of an exemplary scan magnet circuit with a power amplifier driving an inductive scan magnet.
Figure 11B:
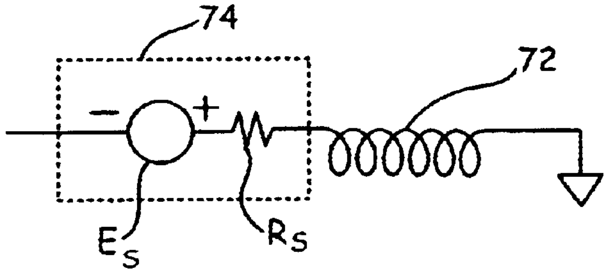
FIG. 11B is a schematic diagram of an exemplary scan magnet circuit with a scan magnet driver modeled as a Thevenin source consisting of a voltage source and a series resistance.
Figure 11C:
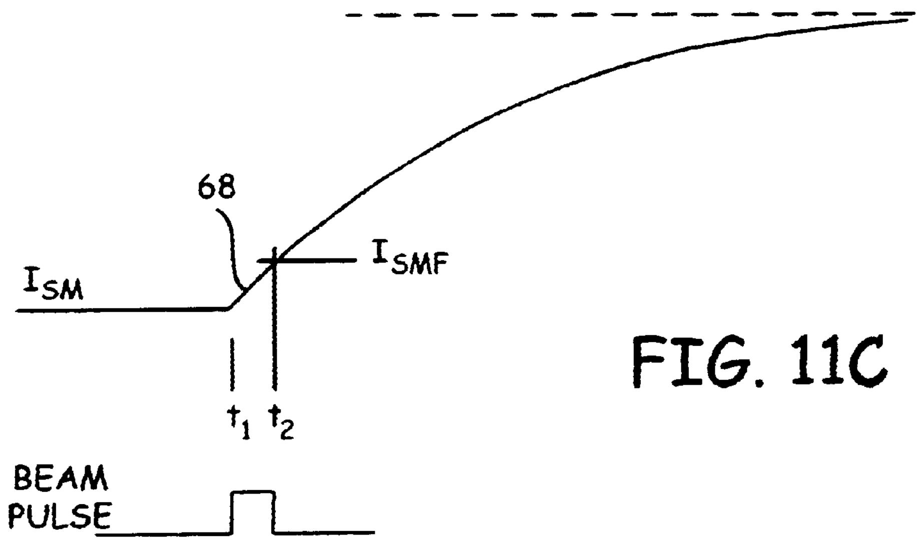
FIG. 11C is a graph illustrating the exponential increase in the scan magnet current for a step increase in the voltage source connected thereto.

Similarly, the magnitude of the vertical deflection sweep H may be changed by changing the slope of the deflection magnet current $I_{SM}$. FIG. 11A is a schematic diagram of an exemplary scan magnet circuit with power amplifier 70 driving inductive scan magnet 72. FIG. 11B is a schematic diagram of an exemplary scan magnet circuit with scan magnet driver 74 modeled as a Thevenin source consisting of a voltage source $E_s$ and a series resistance $R_s$. A step increase in voltage source $E_s$ from an initial steady state value will cause the current $I_{SM}$ in the scan magnet to increase exponentially toward the final value $I_{SMF}$ which is equal to $E_S/R_S$. (The ideal linear slope shown in FIG. 10 is not achievable because of the inability to change the current flowing through an inductor instantaneously.) FIG. 11C is a graph illustrating the exponential increase in sloped region 68 in the scan magnet current $I_{SM}$ for a step increase in the voltage source $E_s$. The exponential function is approximately linear immediately after the step function is initiated, as is illustrated in Table 1.

TABLE 1

| Fraction of Tc | Linear Curve | Exponential Curve | error % |
|---|---|---|---|
| 0.01 | 0.01 | 0.00995 | 0.00 |
| 0.02 | 0.02 | 0.01980 | 0.02 |
| 0.03 | 0.03 | 0.02955 | 0.04 |
| 0.04 | 0.04 | 0.03921 | 0.08 |
| 0.05 | 0.05 | 0.04877 | 0.12 |
| 0.06 | 0.06 | 0.05824 | 0.18 |
| 0.07 | 0.07 | 0.06761 | 0.24 |
| 0.08 | 0.08 | 0.07688 | 0.31 |
| 0.09 | 0.09 | 0.08607 | 0.39 |
| 0.10 | 0.10 | 0.09516 | 0.48 |

Figure 12:
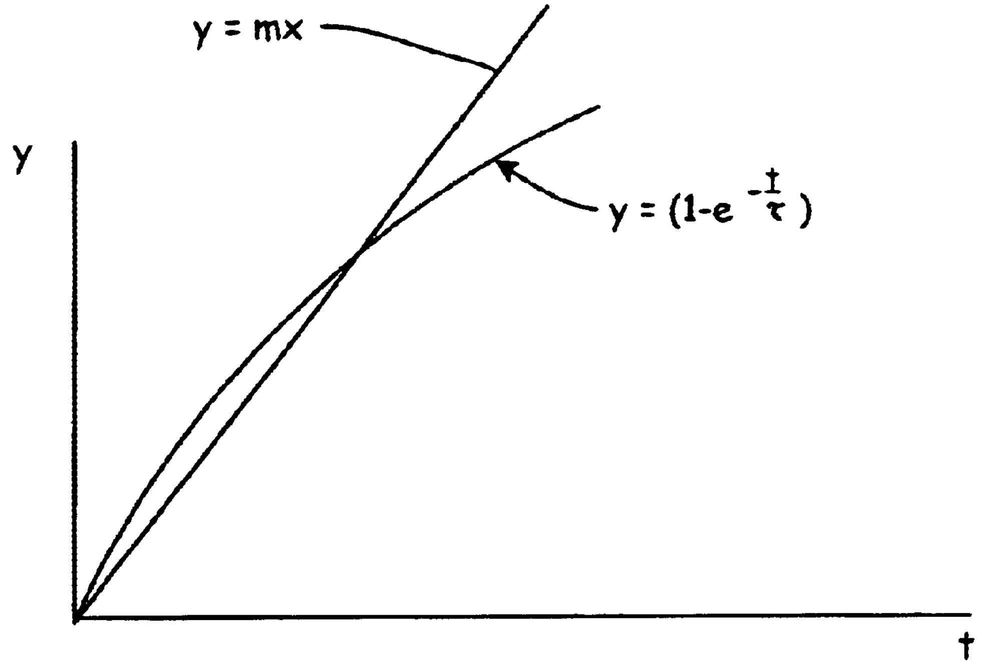
FIG. 12 is a graph illustrating a method of reducing the total error by using a curve fitting estimation for the least error fit with a straight line.

FIG. 12 is a graph illustrating a method of reducing the total error by using a curve fitting estimation for the least error fit with a straight line. Instead of the slope (m) being $E_S/R_S$, the slope (m) may be an approximation that is slightly smaller than $E_S/R_S$. Using a least squares estimation method, the error may be reduced as shown in Table 2.

TABLE 2

| Fraction of Tc | Linear Curve | Exponential Curve | error % | Least Squares Curve Fit | error % |
|---|---|---|---|---|---|
| 0.00 | 0.00 | 0.00000 | 0.00 | 0.000000 | 0.00 |
| 0.01 | 0.01 | 0.00995 | 0.00 | 0.009618 | −0.03 |
| 0.02 | 0.02 | 0.01980 | 0.02 | 0.019236 | −0.06 |
| 0.03 | 0.03 | 0.02955 | 0.04 | 0.028854 | −0.07 |
| 0.04 | 0.04 | 0.03921 | 0.08 | 0.038471 | −0.07 |
| 0.05 | 0.05 | 0.04877 | 0.12 | 0.048089 | −0.07 |
| 0.06 | 0.06 | 0.05824 | 0.18 | 0.057707 | −0.05 |
| 0.07 | 0.07 | 0.06761 | 0.24 | 0.067325 | −0.03 |
| 0.08 | 0.08 | 0.07688 | 0.31 | 0.076943 | 0.01 |
| 0.09 | 0.09 | 0.08607 | 0.39 | 0.086561 | 0.05 |
| 0.10 | 0.10 | 0.09516 | 0.48 | 0.096179 | 0.10 |

Curve fit: m = 0.961787475

Figure 13:
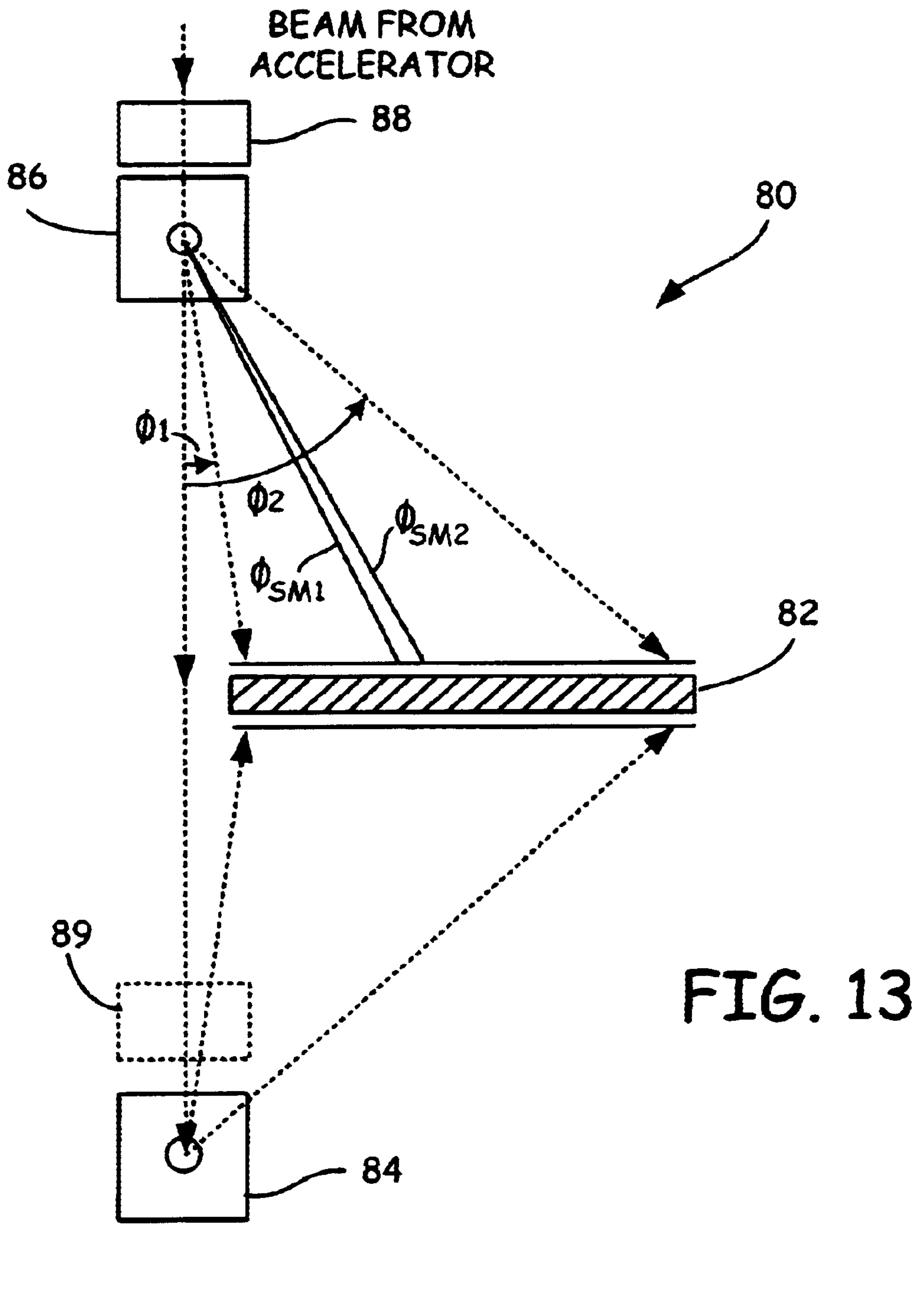
FIG. 13 is a diagram of a two sided irradiation system according to the present invention.

FIG. 13 is a diagram of two sided irradiation system 80 according to the present invention. The top side of material 82 being processed will be exposed to irradiation in a series of overlapping rectangular profiles of the type described in FIG. 7. The location of the profiles and the corresponding overlap may be established in advance by a location and calibration method under computer control. This calibration method may employ a sensor that provides an indication of the actual profile position either at the surface of the material being processed or at the exit through the material being processed. In either case, the computer control system may determine the actual deflection currents necessary to locate the rectangular profiles and their overlap as shown in FIG. 8. The control computer may further periodically verify this position control with a self-test function to account for any drift or variations in the electronic control and drive circuits.

The actual locations of the profiles, as shown in FIG. 13, are a geometric function. In general, the deflection of each electron stripe will be in an angular amount proportional to the deflection magnet current. This position must be converted to a linear displacement in the plane of the material being processed by the use of a trigonometric arc tangent function In similar fashion, the bottom side of the material being processed will be exposed to irradiation in a series of rectangular profiles. Lower deflection magnet 84 of FIG. 13 may be controlled in either of two possible ways. A first control method is to establish a relatively constant deflection current in lower deflection magnet 84 which directs the incoming electron stripe toward a particular location on the bottom side of material 82, with the rectangular intensity profile formed into a calibrated rectangular shape by driving upper deflection magnet 86 appropriately, as described above with respect to FIGS. 10–12. The second control method is to deactivate upper deflection magnet 86 to allow the incoming electron stripe to pass through undeflected, and drive lower deflection magnet 84 to form the rectangular intensity profile directed to the bottom side of material 82 being processed. The former method has the benefit that only one magnet drive subsystem need have a carefully managed dynamic drive capability. The benefit of the latter method is that higher precision may be more easily achieved. This managed drive capability may involve a combination of the response characteristics of the magnet drive amplifier and the control computer, or it may be completely contained within a more complex magnet drive subsystem that may contain a computer or other type of calibrated controller.

The computer control of the beam manipulation system of FIG. 13 involves control of the magnet drive currents for each of the three magnets (duopole magnet 88, upper deflection magnet 86 and lower deflection magnet 84) for each pulsed electron beam from the accelerator. In all cases, an appropriate and calibrated current must be established in duopole 88 magnet to control the angle of divergence of the spot. For top side exposure, the position and deflection characteristics are determined solely by the dynamic drive of upper deflection magnet 86. In order to expose all of material 82, the current provided to upper deflection magnet 86 must be controlled in a range that yields deflection angles between $\phi_1$ and $\phi_2$. For the sweep of each individual profile, the current provided to upper deflection magnet 86 is controlled to slope between values that yield deflection angles $\phi_{SM1}$ and $\phi_{SM2}$. For bottom side exposure, all three magnets must be controlled in a similar manner as described above.

In an alternative embodiment, optional second duopole magnet 89 may be provided as part of the lower magnet structure. In this embodiment, the electron beam from the accelerator is formed into a stripe by duopole magnet 88 for exposing the upper side of material 82 only. The electron beam is also passed on to duopole magnet 89 to form a stripe for exposing the lower side of material 82. The upper stripe formed by duopole magnet 88 is swept and directed onto material 82 by upper deflection magnet 86, and the lower stripe formed by duopole magnet 89 is swept and directed onto material 82 by lower deflection magnet 84. Other variations in the configurations and functions of the magnets may be made while following the teachings of the present invention.

The present invention therefore provides an irradiation system in which material is exposed on two opposite sides with a precisely controllable, uniform dosage of radiation. In an exemplary embodiment, an electron beam is formed into a rectangular intensity distribution profile, and overlap of successive profiles is controlled to yield a consistent dose pattern delivered to the material being processed. As a result, performance of the system is improved over that of the prior art with a relatively simple set of magnets and controls.

Although the present invention has been described with reference to preferred embodiments, workers skilled in the art will recognize that changes may be made in form and detail without departing from the spirit and scope of the invention.

What is claimed is:

1. A method of providing irradiation to material from an electron beam providing source, comprising:

operating on the electron beam to construct a profile that includes successive electron beam pulses, has an intensity distribution in a first dimension that decreases with increased distance from a center point, and has an intensity distribution in a second dimension that is substantially uniform; and deflecting the profile onto a first side of the material in a first pattern with substantial overlap in the first dimension and without substantial overlap in the second dimension.

2. The method of claim 1, further comprising:

deflecting the profile onto a second side of the material in a second pattern with substantial overlap in the first dimension and without substantial overlap in the second dimension.

3. The method of claim 1, wherein the step of operating on the electron beam to construct a profile comprises:

passing the electron beam through a magnet structure to define a stripe having a horizontal width; and performing a vertical sweep to move the stripe a predetermined distance in the vertical direction.

4. The method of claim 3, wherein the first dimension is horizontal and the second dimension is vertical.

5. The method of claim 3, wherein the step of performing a vertical sweep comprises:

initiating an electron beam pulse to generate the electron beam; and during the electron beam pulse, altering a current provided to a deflection magnet to move the stripe in the vertical direction.

6. The method of claim 5, wherein the current provided to the deflection magnet is altered according to an exponential function.

7. The method of claim 6, wherein the exponential function is statistically fit to a linear function.

8. A method of providing irradiation to material from first and second opposite sides with a single electron beam providing source, comprising:

spreading the electron beam into a stripe having an expanded horizontal width with a horizontal intensity distribution that decreases along the width of the stripe with increased distance from a center of the stripe;

deflecting the stripe with an upper deflection magnet in a vertical sweep to create a profile having a vertical intensity distribution profile that is substantially uniform;

deflecting the profile with the upper deflection magnet to impinge on the first side of the material in a first pattern with substantial overlap horizontally and without substantial overlap vertically; and deflecting the profile with a lower deflection magnet to impinge on the second side of the material in a second pattern with substantial overlap horizontally and without substantial overlap vertically.

9. The method of claim 8, wherein the step of deflecting the stripe with the upper deflection magnet in a vertical sweep comprises:

initiating an electron beam pulse to generate the electron beam; and during the electron beam pulse, altering a current provided to the upper deflection magnet to vertically move the stripe.

10. The method of claim 9, wherein the current provided to the upper deflection magnet is altered according to an exponential function.

11. The method of claim 10, wherein the exponential function is statistically fit to a linear function.

12. A method of providing irradiation to material from first and second opposite sides with a single electron beam providing source, comprising:

spreading the electron beam into a stripe having an expanded horizontal width with a horizontal intensity distribution that decreases along the width of the stripe with increased distance from a center of the stripe;

deflecting the stripe with an upper deflection magnet in a vertical sweep to create a first profile having a vertical intensity distribution that is substantially uniform;

deflecting the first profile with the upper deflection magnet to impinge on the first side of the material in a first pattern with substantial overlap horizontally and without substantial overlap vertically;

deflecting the stripe with a lower deflection magnet in a vertical sweep to create a second profile having a vertical intensity distribution that is substantially uniform; and deflecting the second profile with the lower deflection magnet to impinge on the second side of the material in a second pattern with substantial overlap horizontally and without substantial overlap vertically.

13. The method of claim 12, wherein the steps of deflecting the stripe with the upper deflection magnet in a vertical sweep and deflecting the stripe with the lower deflection magnet in a vertical sweep each comprise:

initiating an electron beam pulse to generate the electron beam; and during the electron beam pulse, altering a current provided to a respective deflection magnet to vertically move the stripe.

14. The method of claim 13, wherein the current provided to the respective deflection magnet is altered according to an exponential function.

15. The method of claim 14, wherein the exponential function is statistically fit to a linear function.

16. A system for providing irradiation to material from first and second opposite sides, comprising:

an accelerator for providing an accelerated electron beam;

a magnet structure for spreading the electron beam into a stripe having an expanded horizontal width with a horizontal intensity distribution that decreases along the width of the stripe with increased distance from a center of the stripe;

an upper deflection magnet operable to deflect the stripe in a vertical sweep to create a profile having a vertical intensity distribution that is substantially uniform and to direct the profile onto the first side of the material in a first pattern with substantial overlap horizontally and without substantial overlap vertically;

a lower deflection magnet operable to direct the profile onto the second side of the material in a second pattern with substantial overlap horizontally and without substantial overlap vertically.

17. The system of claim 16, further comprising:

a controller operatively connected to the upper deflection magnet to provide a changing current to the upper deflection magnet to perform the vertical sweep of the stripe.

18. The system of claim 17, wherein the controller is operable to provide an exponentially changing current to the upper deflection magnet to perform the vertical sweep of the stripe.

19. The system of claim 18, wherein the exponentially changing current is statistically fit to a linear function.

20. A system for providing irradiation to material from first and second opposite sides, comprising:

an accelerator for providing an accelerated electron beam;

a magnet structure for spreading the electron beam into a stripe having an expanded horizontal width with a horizontal intensity distribution that decreases along the width of the stripe with,increased distance from a center of the stripe;

an upper deflection magnet operable to deflect the stripe in a vertical sweep to create a first profile having a vertical intensity distribution that is substantially uniform and to direct the profile onto the first side of the material in a first pattern with substantial overlap horizontally and without substantial overlap vertically;

a lower deflection magnet operable to deflect the stripe in a vertical sweep to create a second profile having a vertical intensity distribution that is substantially uniform and to direct the second profile onto the second side of the material in a second pattern with substantial overlap horizontally and without substantial overlap vertically.

21. The system of claim 20, further comprising:

a controller operatively connected to the upper deflection magnet and the lower deflection magnet to provide a changing current to the upper deflection magnet and the lower deflection magnet to perform the vertical sweeps of the stripe.

22. The system of claim 21, wherein the controller is operable to provide an exponentially changing current to the upper deflection magnet and the lower deflection magnet to perform the vertical sweeps of the stripe.

23. The system of claim 22, wherein the exponentially changing current is statistically fit to a linear function.

24. A method of providing irradiation to material from first and second opposite sides with a single electron beam providing source, comprising:

spreading the electron beam into a first stripe having an expanded horizontal width with a horizontal intensity distribution that decreases along the width of the first stripe with increased distance from a center of the first stripe;

deflecting the first stripe with an upper deflection magnet in a vertical sweep to create a first profile having a vertical intensity distribution profile that is substantially uniform;

deflecting the first profile with the upper deflection magnet to impinge on the first side of the material in a first pattern with substantial overlap horizontally and without substantial overlap vertically;

spreading the electron beam into a second stripe having an expanded horizontal width with a horizontal intensity distribution that decreases along the width of the second stripe with increased distance from a center of the second stripe;

deflecting the second stripe with a lower deflection magnet in a vertical sweep to create a second profile having a vertical intensity distribution profile that is substantially uniform; and deflecting the second profile with the lower deflection magnet to impinge on the second side of the material in a second pattern with substantial overlap horizontally and without substantial overlap vertically.

25. A system for providing irradiation to material from first and second opposite sides, comprising:

an accelerator for providing an accelerated electron beam;

an upper magnet structure for spreading the electron beam into a first stripe having an expanded horizontal width with a horizontal intensity distribution that decreases along the width of the first stripe with increased distance from a center of the first stripe;

an upper deflection magnet operable to deflect the first stripe in a vertical sweep to create a first profile having a vertical intensity distribution that is substantially uniform and to direct the first profile onto the first side of the material in a first pattern with substantial overlap horizontally and without substantial overlap vertically;

a lower magnet structure for spreading the electron beam into a second stripe having an expanded horizontal width with a horizontal intensity distribution that decreases along the width of the second stripe with increased distance from a center of the second stripe;

a lower deflection magnet operable to deflect the second stripe in a vertical sweep to create a second profile having a vertical intensity distribution that is substantially uniform and to direct the second profile onto the second side of the material in a second pattern with substantial overlap horizontally and without substantial overlap vertically.

* * * * *

UNITED STATES PATENT AND TRADEMARK OFFICE

CERTIFICATE OF CORRECTION

PATENT NO. : 6,683,319 B1
DATED : January 27, 2004
INVENTOR(S) : Steven E. Koenck et al.

It is certified that error appears in the above-identified patent and that said Letters Patent is hereby corrected as shown below:

Title page,
Item [56], References Cited, U.S. PATENT DOCUMENTS, delete "3,676,678", insert -- 3,676,675 --

Column 11,
Line 28, delete "with," insert -- with --

Signed and Sealed this

Fourteenth Day of September, 2004

JON W. DUDAS
*Director of the United States Patent and Trademark Office*